United States Patent [19]

George et al.

[11] Patent Number: 4,904,670
[45] Date of Patent: Feb. 27, 1990

[54] PYRIDINE DERIVATIVES HAVING ANXIETY STATE OR SLEEP THEREAPEUTIC PROPERTIES

[75] Inventors: Pascal George, Vitry sur Seine; Claudie Giron, Antony, both of France

[73] Assignee: Synthelabo, Paris, France

[21] Appl. No.: 196,621

[22] Filed: May 19, 1988

[30] Foreign Application Priority Data

May 21, 1987 [FR] France ................... 87 07125

[51] Int. Cl.$^4$ ................... A61K 31/445; C07D 471/02
[52] U.S. Cl. ................... 514/300; 546/121
[58] Field of Search ................... 546/121; 514/300

[56] References Cited

U.S. PATENT DOCUMENTS 4,767,755  8/1988  George et al. ................... 546/121

FOREIGN PATENT DOCUMENTS 0172096  2/1986  European Pat. Off. ............ 540/524
2593817  8/1987  France ................... 546/121

Primary Examiner—Mary C. Lee
Assistant Examiner—Robert C. Whittenbaugh
Attorney, Agent, or Firm—Wegner & Bretschneider

[57] ABSTRACT

A compound of formula

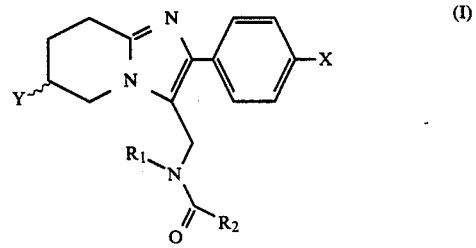

in which:
X denotes hydrogen or a halogen, a $C_1$-$C_4$ alkoxy group or a $C_1$-$C_6$ alkyl group;
Y denotes hydrogen or a methyl group;
$R_1$ denotes a $C_1$-$C_4$ alkyl group; and
$R_2$ denotes a $C_1$-$C_6$ alkyl group;
or an addition salt thereof with a pharmacologically acceptable acid.

4 Claims, No Drawings

PYRIDINE DERIVATIVES HAVING ANXIETY STATE OR SLEEP THEREAPEUTIC PROPERTIES

The present invention relates to 3-acylamino-methyl-5,6,7,8-tetrahydroimidazo[1,2-a]pyridine derivatives, their preparation and their use in therapy.

The present invention provides a compound of formula

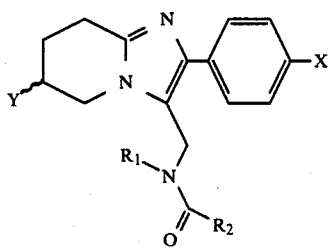

(I)

in which:
x denotes hydrogen or a halogen, a $C_1$–$C_4$ alkoxy group or a $C_1$–$C_6$ alkyl group;
Y denotes hydrogen or a methyl group;
$R_1$ denotes a $C_1$–$C_4$ alkyl group; and
$R_2$ denotes a $C_1$–$C_6$ alkyl group;
or an addition salt thereof with a pharmacologically acceptable acid.

When Y denotes a methyl group, the carbon atom bearing it is asymmetric. The compound of the invention may hence be in the form of a pure enantiomer or a mixture thereof.

The preferred compounds are those in which X denotes chlorine or a methyl group, $R_1$ denotes a methyl group and $R_2$ denotes an n-propyl or isobutyl group.

The present invention also provides a process for the preparation of a compound of formula (I) which comprises catalytically hydrogenating, under pressure, an analogue of a compound of formula (I) which is unsaturated at the 5-, 6-, 7- and 8-positions. These compounds are described in U.S. No. 4,650,796.

The hydrogenation may be performed, for example, in the presence of palladium or rhodium absorbed on a support such as charcoal or alumina. The starting compound may, for example, be in the form of a base or a salt, for example a hydrochloride. It may also be present in a solvent such as an aliphatic alcohol, for example methanol or ethanol, or an acidic solvent such as acetic acid.

The present invention also provides a pharmaceutical composition comprising a compound of formula (I) and an excipient. The compositions may be in any form suitable for oral or parenteral administration, for example in the form of tablets, dragees, gelatin capsules, solutions to be taken by mouth or injectable solutions. The daily dose may, for example, vary from 0.1 to 100 mg.

The present invention also provides a compound of formula (I) for use in a method of treatment of the human or animal body by therapy.

The present invention further provides a compound of formula (I) for use in in a method of treatment of anxiety states, sleep disorders, behavioural disorders attributable to cerebral vascular damage or cerebral sclerosis, temporary loss of consciousness due to cranial trauma, metabolic encephalopathies, thrombosis, tumours or states requiring immunomodulatory agents or platelet activation factor antagonists.

The Examples which follow further illustrate the present invention. Microanalysis and the IR and NMR spectra confirm the structures of the products obtained.

EXAMPLE 1

N-[{2-(4-Methylphenyl)-6-methyl-5,6,7,8-tetrahydroimidazo[1,2-a]pyridin-3-yl}methyl]-N,3-dimethylbutanamide hydrochloride 1 g (2.86 mmol) of N-[{2-(4-methylphenyl)-6-methylimidazo[1,2-a]pyridin-3-yl}methyl]-N-3-dimethylbutanamide is dissolved in 29 ml of 0.1N hydrogen chloride in isopropyl alcohol. 50 ml of isopropyl alcohol and 0.5 g of palladinized charcoal (10% palladium) are added and the mixture is hydrogenated under approximately 0.35 MPa (50 PSI) pressure for 8 hours.

The catalyst is filtered off, the solvent is evaporated off under reduced pressure and the residue is treated with ether. 0.8 g of the expected product is obtained in the form of the hydrochloride.

M.p. 195°–196° C.

EXAMPLE 2

N-[{2-(4-Hexylphenyl)-6-methyl-5,6,7,8-tetrahydroimidazo[1,2-a]pyridin-3-yl}methyl]-N,3-dimethylbutanamide hydrochloride 3.53 g (8.4 mmol) of N-[{2-(4-hexylphenyl)-6-methylimidazo[1,2-a]pyridin-3-yl}methyl]-N-3-dimethylbutanamide hydrochloride is dissolved in 64 ml of 95% pure ethanol containing 1.5 g of palladinized charcoal (10% palladium). The mixture is hydrogenated under a pressure of approximately 0.35 MPa (50 PSI) until 2 mol of hydrogen have been absorbed. The catalyst is removed by filtration and the solvent evaporated off under reduced pressure. The residue is dissolved in dichloromethane and the insoluble material removed by filtration. The filtrate is concentrated under reduced pressure and the residue washed with ether. 3.03 g of a white solid are obtained.

M.p. 161°–162° C.

EXAMPLE 3

N-[{2-(4-Chlorophenyl)-6-methyl-5,6,7,8-tetrahydroimidazo[1,2-a]pyridin-3-yl}methyl]-N,3-dimethylbutanamide hydrochloride.

3 g (8.1 mmol) of N-[{2-(4-chlorophenyl)-6-methylimidazo[1,2-a]pyridin-3-yl}methyl]-N,3-dimethylbutanamide hydrochloride is dissolved in 200 ml of acetic acid, 0.7 g of rhodium on alumina (5% rhodium) is added and the mixture is hydrogenated under a pressure of approximately 0.35 MPa (50 PSI) until absorption is complete. The catalyst is removed by filtration and the solvent evaporated off under reduced pressure. The residue is taken up with dichloromethane and the solution washed with bicarbonate water. The organic phase is separated after settling and dried over magnesium sulphate. After filtration and evaporation of the solvent, a solid residue is taken up with ether and purified by chromatography on a silica column. The hydrochloride is prepared therefrom in 0.1N hydrogen chloride in isopropyl alcohol. 1.55 g of the expected product is obtained.

M.p. 197°–198° C.

The table below illustrates the structures and physical properties of some compounds according to the invention.

TABLE (I)

| N° | X | Y | $R_1$ | $R_2$ | M.p. (°C.) |
|---|---|---|---|---|---|
| 1 | Cl | H | $CH_3$ | $i-C_4H_9$ | 193–195* |
| 2 | $n-C_3H_7$ | H | $CH_3$ | $i-C_4H_9$ | 197–199* |
| 3 | Cl | $CH_3$ | $CH_3$ | $nC_3H_7$ | 194–196* |
| 4 | Cl | $CH_3$ | $CH_3$ | $i-C_4H_9$ | 197–198* |
| 5 | $CH_3$ | $CH_3$ | $CH_3$ | $i-C_4H_9$ | 195–196* |
| 6 | $C_2H_5$ | $CH_3$ | $CH_3$ | $i-C_4H_9$ | 196–198* |
| 7 | $n-C_3H_7$ | $CH_3$ | $CH_3$ | $i-C_4H_9$ | 184–186* |
| 8 | $n-C_6H_{13}$ | $CH_3$ | $CH_3$ | $i-C_4H_9$ | 161–163* |
| 9 | $OCH_3$ | H | $CH_3$ | $i-C_4H_9$ | 173–175* |

*hydrochloride

The compounds of the invention were subjected to pharamacological tests to demonstrate their therapeutic activity.

ACUTE TOXICITY

The $LD_{50}$ (50% lethal dose) values are greater than or equal to 300 mg/kg in mice when administered orally.

ANTAGONISM WITH RESPECT TO CARDIAZOL (TRADE MARK) INDUCED CLONIC CONVULSIONS IN MICE

The test is modelled on that described in Goodman et al., J. Pharm. Exp. Ther., (1953), 08, 168–176. The mice receive the product to be tested, or the solvent alone, intraperitoneally, 30 minutes (intraperitoneal route) or 60 minutes (oral route) before the intravenous injection of 35 mg/kg of Cardiazol. The animals are then observed for one hour and, for each batch, the percentage of mice displaying clonic convulsions is noted (100% of clonic convulsions and 10 to 20% of tonic convulsions in the control animals).

For each dose, the percentage protection relative to the control animals is calculated, which enables the $AD_{50}$, the dose which protects 50% of the animals against the convulsant effects of Cardiazol, to be determined graphically.

The $AD_{50}$ values of the compounds of the invention are from 0.1 to 10 mg/kg intraperitoneally and from 1 to 100 mg/kg orally.

ACTION ON THE ELECTROCORTICOGRAM OF VENTILATED CURARIZED RATS

The sedative or hypnotic activity of the compounds is determined by observing their action on the electrocorticogram of rats according to the method described in H. Depoortere, Rev. E.E.G. Neurophysiol., 10, 3, 207–214 (1980) and in H. Depoortere and M. Decobert, J. Pharmacol. (Paris), 14, 2, 195–265 (1983).

The test products are administered intraperitoneally at increasing doses of from 1 to 30 mg/kg. They induce sleep traces at and above doses of from 0.1 to 3 mg/kg.

EFFECTS ON SODIUM 4-HYDROXYBUTYRATE-INDUCED "SLEEP" TIME

This action is determined by observing the influence of the compounds on the sodium 4-hydroxybutyrate-induced "sleep" time in curarized rats.

The animals used are Charles River strain male rats weighing 200±20 g. The animals, curarized with alloferin administered i.p. in a proportion of 1 mg/kg, are placed under artificial respiration using a mask applied on the muzzle (respiratory rate=50/minute; respiratory volume=14 ml).

The oesophagus is ligatured beforehand in order to avoid entry of air into the stomach.

Frontoparietal and occipital cortical electrodes enable the electrocorticographic activity to be recorded on a Grass (Trade Mark) model 79 P polygraph at a rate of 6 mm/sec.

The preparation of the animal is performed under local anaesthesia (2% strength xylocaine). The rats are maintained at a constant temperature of 37.5° C. throughout the experiment. Ten minutes after the preparation of the rat is complete, a dose of 200 mg/kg of sodium 4-hydroxybutyrate is injected intravenously into the tail.

A dose of 10 mg/kg of the test compound is administered intraperitoneally 3 minutes after the administration of the sodium 4-hydroxybutyrate.

The assessment of the traces is carried out every 15 minutes for 75 minutes after the injection of sodium 4-hydroxybutyrate. The total "sleep" time is determined for this period. A series of 15 controls enables the sodium 4-hydroxybutyrate-induced "sleep" time to be defined accurately.

A statistical analysis of the results is carried out using the Mann-Whitney "U" test.

Some compounds reduce the effect of sodium 4-hydroxybutyrate (up to a 23% decrease in the sleep time at a dose of 1 mg/kg), while others potentiate these effects (up to a 38% increase at a dose of 10 mg/kg). The effect can be opposite according to whether the compounds are administered at high or low doses.

These tests show that the compounds of the invention possess anxiolytic, sleep-inducing, hypnotic and anticonvulsant properties; they are hence useful for the treatment of anxiety states, sleep disorders and other neurological and psychiatric conditions, for the treatment of disorders of alertness, especially for combating behavioural disorders attributable to cerebral vascular damage and to cerebral sclerosis in geriatrics, and also for the treatment of temporary loss of consciousness due to cranial trauma and for the treatment of metabolic encephalopathies.

Moreover, by virtue of their affinity for peripheral benzodiazepine receptors, the compounds of the invention are also immunomodulatory, antithrombotic and antitumour agents and platelet activation factor (PAF) antagonists.

We claim:

1. A compound of formula

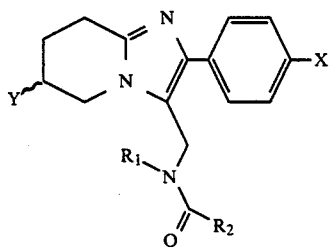

in which:

X is hydrogen or a halogen, a $C_1$–$C_4$ alkoxy group or a $C_1$–$C_6$ alkyl group;

Y is hydrogen or a methyl group;

$R_1$ is a $C_1$–$C_4$ alkyl group; and $R_2$ is a $C_1$–$C_6$ alkyl group;

or an addition salt thereof with a pharmacologically acceptable acid.

2. A compound according to claim 1, wherein X is chlorine or a methyl group, $R_1$ is a methyl group and $R_2$ is an n-propyl or isobutyl group.

3. A pharmaceutical composition for the treatment of convulsions, anxiety states and sleep disorders comprising an effective amount of a compound as defined in claim 1 and an excipient.

4. A method of treatment of a subject suffering from convulsing anxiety states or sleep disorders or liable to suffer therefrom, which comprises administering to the subject an effective amount of the compound as defined in claim 1.

* * * * *